United States Patent
Crumb et al.

[11] Patent Number: 6,030,943
[45] Date of Patent: Feb. 29, 2000

[54] DEHYDRODIDEMNIN B AS AN L-TYPE CALCIUM CHANNEL ENHANCER

[76] Inventors: William J. Crumb, 610 Phosphor Ave., Metairie, La. 70005; Glynn T. Faircloth, 10 Rogers St. #2, River Ct., Cambridge, Mass. 02142

[21] Appl. No.: 09/073,288

[22] Filed: May 6, 1998

Related U.S. Application Data

[60] Provisional application No. 60/045,803, May 7, 1997.

[51] Int. Cl.[7] .............................. A61K 38/00; C07K 5/00; C07K 7/00; C07K 16/00
[52] U.S. Cl. .................... 514/9; 514/11; 530/317
[58] Field of Search ............................ 514/11, 9; 530/317

[56] References Cited

U.S. PATENT DOCUMENTS 5,580,871  12/1996  Earl ...................................... 514/235.8

*Primary Examiner*—Douglas W. Robinson
*Assistant Examiner*—S. G. Marshall
*Attorney, Agent, or Firm*—Ernest V. Linek

[57] ABSTRACT

This invention relates to a new use discovered for the compound known as Aplidine (dehydrodidemnin B) which has the following structure:

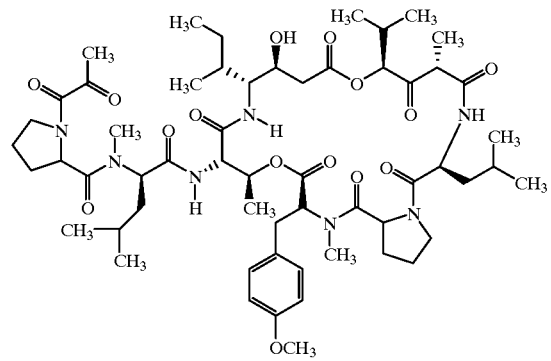

Aplidine has been found to be a potent L-type calcium channel enhancer in the human heart. This effect makes Aplidine a very useful drug for the treatment of congestive heart failure, as well as useful for the treatment of atrial fibrillation.

22 Claims, 2 Drawing Sheets

DEHYDRODIDEMNIN B AS AN L-TYPE CALCIUM CHANNEL ENHANCER

CROSS-REFERENCE TO RELATED APPLICATIONS

This application claims the benefit of U.S. Provisional Application Ser. No. 60/045,803, filed May 7, 1997. The isolation of natural Aplidine (or dehydrodidemnin B) is described in copending application Ser. No. 08/280,110. The disclosures of these applications are hereby incorporated herein by reference.

BACKGROUND OF THE INVENTION

Congestive heart failure (CHF) is one of the leading diagnoses in all hospitalized adults. It is estimated that between 2–3 million adults have CHF in the U.S. with approximately 500,000 new cases diagnosed each year. Currently, approximately 11% of all adults over the age of 65 have CHF. CHF is the most costly disease in managed care with annual expenditures related to CHF exceeding $10 billion. Although available therapies can provide considerable improvement for some patients, morbidity and mortality remain high. With a five-year mortality rate that exceeds many cancers and a two-year mortality rate, which claims the lives of 50% of the patients diagnosed with the disease, CHF is clearly a major health problem.

The therapeutic goal for CHF is to make the cardiac muscle pump more efficiently. This is currently achieved by reducing the work of the heart (ACE inhibitors, vasodilators, diuretics and β-adrenergic blockers) and/or increasing myocardial contractility (digoxin and phosphodiesterase inhibitors). Unfortunately, current inotropic therapy for the failing heart is associated with major limitations: digoxin and the phosphodiesterase inhibitors are associated with life-threatening toxicity and β blockers become less effective inotropic compounds as heart failure progresses. Some of the cellular changes that occur in hear failures are summarized in Table 1.

TABLE 1

| | |
|---|---|
| Ca current density | ↔ |
| cAMP content | ↓ |
| β-AR | ↓ |
| SR Ca channel | ↓ |
| stimulated AC | ↓ |

β-AR, β adrenergic receptor; AC, adenylate cyclase;
SR Ca channel, sarcoplasmic Ca release channel One promising approach to inotropic therapy is modulation of cardiac ion channels. As indicated in Table 1, the density of calcium channels does not change in the failing human heart making it a plausible target for inotropic therapy. It is through these channels that calcium ($Ca^{2+}$) ions enter the cardiac myocyte to elicit excitation-contraction and pumping of blood out of the ventricles.

The regulation of extracellular calcium plays a crucial role in the treatment of several cardiovascular disorders. The most common agents used to regulate calcium ions are calcium antagonists or calcium channel blockers. In essence, these compounds "slow" the entry of calcium ions into the cell and thereby reduce the force or contractility of cardiac muscle resulting in the lowering of blood pressure. Additionally, these agents find use in the treatment of angina caused by abnormal vasoconstriction of coronary arteries and classical effort associated angina.

A smaller class of agents that regulate calcium ions are calcium agonists or calcium channel enhancers. These compounds promote the movement of calcium ions through the cell wall and therefore increase contractility. Such compounds may be useful in the treatment of disorders of lessened cardiac output such as congestive heart failure. Alternatively, they may be used as tools in the pharmacological study of calcium channels. One problem typically encountered in the use of calcium channel enhancers is their elevating effect on blood pressure. Surprisingly, it has been discovered that while Aplidine is a very effective calcium channel enhancer, it has no effect on blood pressure.

SUMMARY OF THE INVENTION

This invention relates to a new use discovered for the compound known as Aplidine (dehydrodidemnin B) which has the following structure:

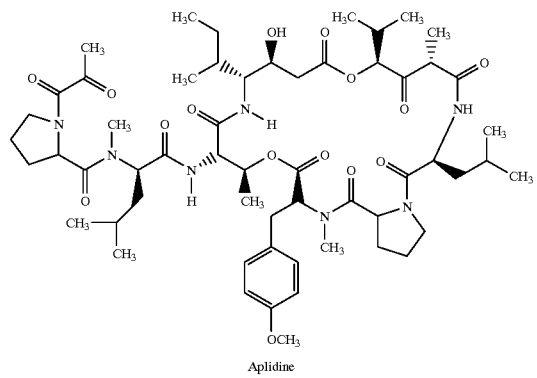

Aplidine

Aplidine has been found to be a potent L-type calcium channel enhancer in the human heart. This effect makes Aplidine a very useful drug for the treatment of congestive heart failure, as well as useful for the treatment of atrial fibrillation. It is likewise believed that synthetic analogs and derivatives of Aplidine will also possess this utility.

Aplidine will exhibit beneficial cardiovascular activities such as increasing cardiac contractibility, decreasing heart rate, decreasing vascular resistance, decreasing rate pressure product (as an index of oxygen consumption) or producing class III antiarrhythmic activity. This pharmacological profile makes Aplidine useful in cardiovascular diseases such as congestive heart failure.

Also disclosed and claimed herein is a method of treating congestive heart failure in a mammal in need thereof by administering to said mammal an effective amount of Aplidine. Further, pharmaceutical formulations for use in treating congestive heart failure are provided comprising an effective amount of Aplidine, or a pharmaceutically acceptable salt thereof, in admixture with one or more pharmaceutically acceptable carriers, diluents or excipients. If desired, additional active ingredients may be administered with Aplidine, for example, beta-adrenergic receptor agonists, phosphodiesterase inhibitors, or the like.

Other therapeutic methods of treatment using the compound dehydrodidemnin B (or Aplidine) include the following:

(a) Producing a cardiotonic effect in a patient by administering the compound dehydrodidemnin B or a pharmaceutically acceptable salt thereof in an amount effective to produce said cardiotonic effect. Such amounts, administered in unit dosage form, may contain from about 0.01 to about 0.4 grams of said compound per kilogram of patient body weight per day, and may optionally include a biologically compatible excipient. Administration may be made parenterally, intravenously, intraperitoneally, intramuscularly, subcutaneously, transdermally, orally, or any combination thereof. If desired, Aplidine may be administered in conjunction with other active ingredients, such as one or more beta-receptor agonists; one or more phosphodiesterase inhibitors; or the like.

(b) Treating congestive heart failure in a patient by administering an effective amount of the compound dehydrodidemnin B or a pharmaceutically acceptable salt thereof in an amount effective to treat congestive heart failure.

(c) Producing cardiotonic activity in a patient by administering an effective cardiotonic amount of a pharmaceutical composition comprising dehydrodidemnin B and a pharmaceutically acceptable carrier, diluent or excipient.

(d) Prolonging the survival from heart failure in a patient suffering from insufficient cardiac contractile function by administering the compound dehydrodidemnin B or a pharmaceutically acceptable salt thereof in an amount effective to improve cardiac contractile function in said patient. Such amounts, administered in unit dosage form, may contain from about 0.01 to about 0.4 grams of said compound per kilogram of patient body weight per day, and may optionally include a biologically compatible excipient. Administration may be made parenterally, intravenously, intraperitoneally, intramuscularly, subcutaneously, transdermally, orally, or any combination thereof. If desired, Aplidine may be administered in conjunction with other active ingredients, such as one or more beta-receptor agonists; one or more phosphodiesterase inhibitors; or the like. If desired, the compounds may be administered as a component of a nutritional product.

(e) Prolonging the survival from heart failure in a patient suffering from cardiac insufficiency by administering the compound dehydrodidemnin B or a pharmaceutically acceptable salt thereof in an amount sufficient to produce a cardiovascular agonist effect in said patient.

(f) Producing a Class III antiarrhythmic effect for the treatment of atrial arrhythmias by administering the compound dehydrodidemnin B or a pharmaceutically acceptable salt thereof in an amount sufficient to produce a cardiovascular agonist effect.

As will be recognized by those skilled in the art, Aplidine may contain one or more asymmetric carbon atoms. The present invention is not limited to any particular isomer but includes all individual isomers as well as all isomeric mixtures and racemates.

DETAILED DESCRIPTION OF THE INVENTION

Figure 1A:
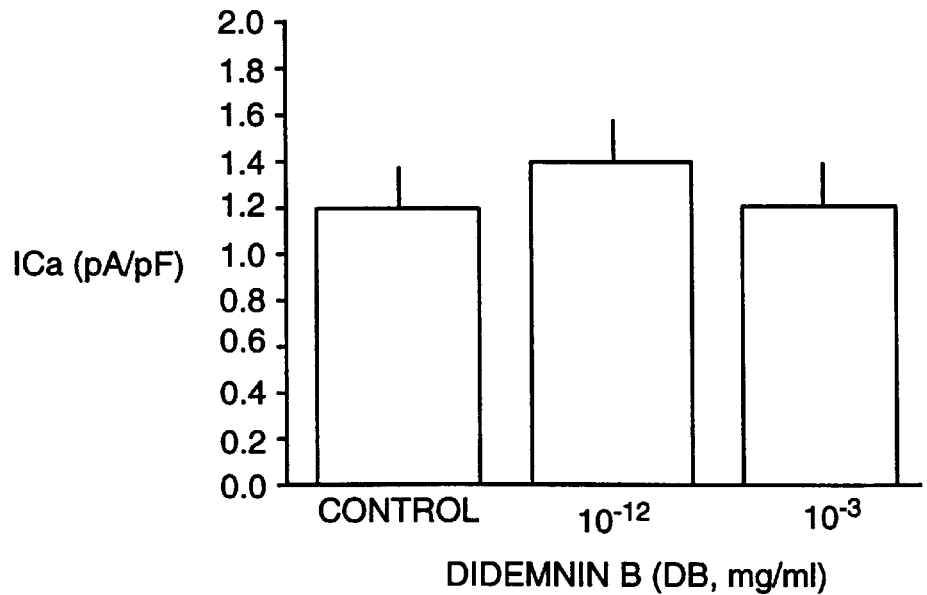
FIGS. 1A and 1B illustrate the interactions of Aplidine (1A) and Didemnin B (DB, 1B) in mg/ml with human atrial calcium current ($I_{Ca}$) measured as the ratio of picoamps (pA) of current to picofarads (pF) as an indication of cell size. The values are normalized because a large current might occur because the cell is larger than the rest.

Aplidine can be isolated from tunicates of the genus Aplidium, and more especially from the species *Aplidium*

*albicans*. The species is found in the Iberian Mediterranean Coast as well as in the Balearic Islands. The species has been also found in Great Britain, English Channel as well as in the Africa Coast and Portugal. It seems to prefer detritic, coralligenic and sciafilae algae communities. They also can be found in more photophilic habitats.

Colonies of the tunicate are generally flat and lobed (2.5 cm diameter). It is jelly like, totally encrusted with sand, which confers a sandy color to the colony. Zooides are of a whitish color 10 mm long; the oral siphon has 6 lobes, and the cloacal languet is trifid, which is a species characteristic. Generally there are 10–11 rows of stigmas. The stomach has 6 marked folds. Gonads are of the family type with one or several ovocites below the digestive track and numerous testicular follicles forming one or double row in the post abdomen. Larvae are incubated in the number of 1 to 9 in the atrial cavity; they have 3 cupping-glasses and several vesicular formations in the anterior part. In a typical procedure, isolation method generally comprises alcoholic extraction of the homogenized tunicate and selective purification of Aplidine. Aplidine can also be prepared by total synthesis, or semisynthetically from Didemnin A, following in both cases standard procedures of protection and activation in peptide chemistry. For example:

Pyruvic acid+L-Pro→Side Chain

Side Chain+Didemnin A→Aplidine

Thus for example, Pro-OBzl, in DMF is mixed with pyruvic acid and HOBt, and DCC in $CH_2Cl_2$ added. The reaction product can be purified and shows the chemical and physical properties corresponding to Pyruvyl-Pro-OBzl. To a solution of this product in $CH_2Cl_2$, EDC and then added. The evaporated residue is purified yielding Aplidine having chemical, physical, spectroscopical and biological characteristics in accord with natural Aplidine.

Aplidine (including any isomeric mixtures) acts as a calcium channel agonists to increase cardiac contractibility. The skilled artisan will appreciate that individual enantiomers may produce better calcium agonist activity such as increasing cardiac contractility and vascular tone than that disclosed herein. These pharmacological activities were examined in the following in vitro model.

Isolation of Human Cardiac Myocytes

Human atrial myocytes were obtained from specimens of human right atrial appendage obtained during surgery from hearts of patients undergoing cardiopulmonary bypass. Tissue samples were quickly immersed in a cardioplegia solution consisting of (in mmol/L): 50 $KH_2PO_4$, 8 $MgSO_4$, 10 $NaHO_3$, 5 adenosine, 25 taurine, 140 glucose, and 100 mannitol, titrated to a pH of 7.4 and bubbled with 100% $O_2$ at 0–4° C. Specimens were then minced into 0.5–1 mm cubes and transferred to a 50 ml conical tube containing an ultra-low calcium wash solution containing (in mmol/L); 137 NaCl, 5 $KH_2PO_4$, 1 $MgSO_4$, 10 taurine, 10 glucose, 5 HEPES, and 100 $\mu$mol/L ($\mu$M) EGTA; pH=7.4 (22–24° C.).

The tissue was next gently agitated by continuous bubbling with 100% $O_2$ for 5 minutes. The tissue was then incubated in 5 ml of solution containing (in mmol/L): 137 NaCl, 5 $KH_2PO_4$, 10 taurine, 10 glucose, 5 HEPES, supplemented with 0.1% bovine albumin, 2.2 mg/ml collagenase type V and 1.0 mg/ml protease type XXIV (Sigma Chemical), pH=7.4 (37° C.) and bubbled continuously with 100% $O_2$. The supernatant was removed after 40 minutes and discarded. The chunks were incubated in a solution of the same ionic composition but supplemented with only collagenase and 100 $\mu$mol/L $CaCl_2$.

Microscopic examination of the medium was performed every 5–10 minutes to determine the number and quality of the isolated cells. When the yield appears to be maximal, the cell suspension was centrifuged for 2 minutes and the resulting pellet was resuspended in a modified Kraftbruhe solution containing (in mmol/L): 25 KCl, 10 $KH_2PO_4$, 25 taurine, 0.5 EGTA, 22 glucose, 55 glutamic acid, and 0.1% bovine albumin, pH=7.3 (22–24° C.). Cells were used within 8 hrs after isolation. Only cells with characteristically normal morphology (rod-shaped, erisp striations, no surface abnormalities) were used.

Electrophysiology

Ionic currents were measured using the whole-cell variant of the patch clamp technique. Pipette-electrodes were freshly manufactured from borosilicate glass using a horizontal pipette puller, and the pipette tips were heat-polished using a microforge. In most experiments, pipettes were pulled to have tip openings of 1–2 $\mu$m, and tip resistances of 1–2M $\Omega$ when filled with internal solution.

Experiments began after ionic current amplitudes and kinetics have stabilized following the onset of intracellular perfusion (typically within 5 minutes after rupturing the membrane patch). Internal and external solutions of different compositions were used to pharmacologically isolate the ionic current(s) of interest from other contaminating currents.

Solutions for Measurement of $I_{ca}$.

Calcium (Ca) currents were measured using an external solution having the composition (in mM): 1.8 $CaCl_2$, 137 NaCl, 20 CsCl, 4 KCl, 1 $MgCl_2$, 10 HEPES, 10 dextrose pH=7.4 with NaOH. The standard internal solution had the composition (in mM): pH=7.4 with NaOH. The standard internal solution had the composition (in mM): 120 CsCl, 20 TEA-Cl, 5 NaCl, 1 $CaCl_2$, 10 EGTA, 10 HEPES, 5 MgATP, 0.2 Na-GTP, adjusted to pH=7.2 with CsOH. Experiments were performed at room temperature (22° C.) to minimize current rundown.

Figure 1B:
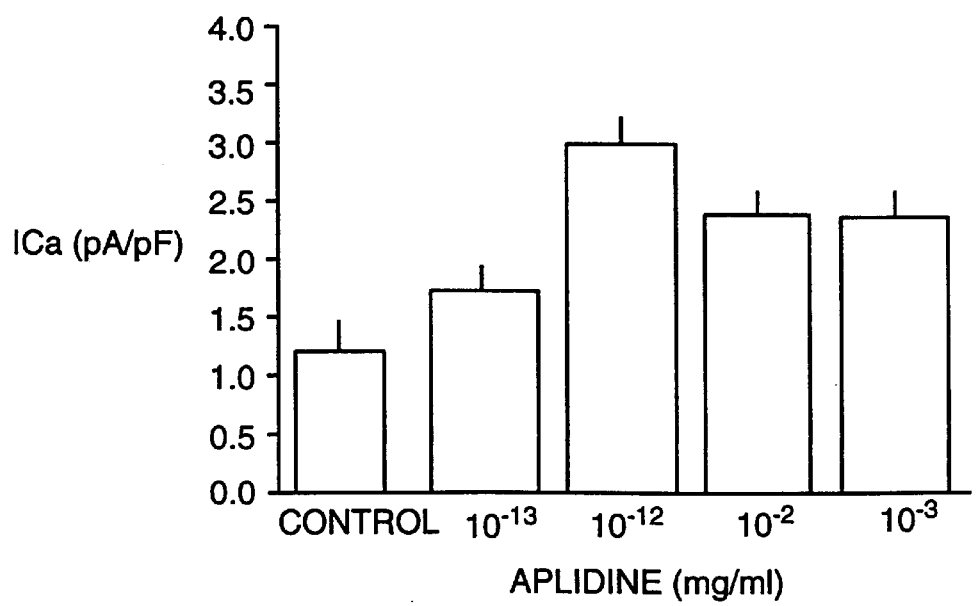
Figure 2:
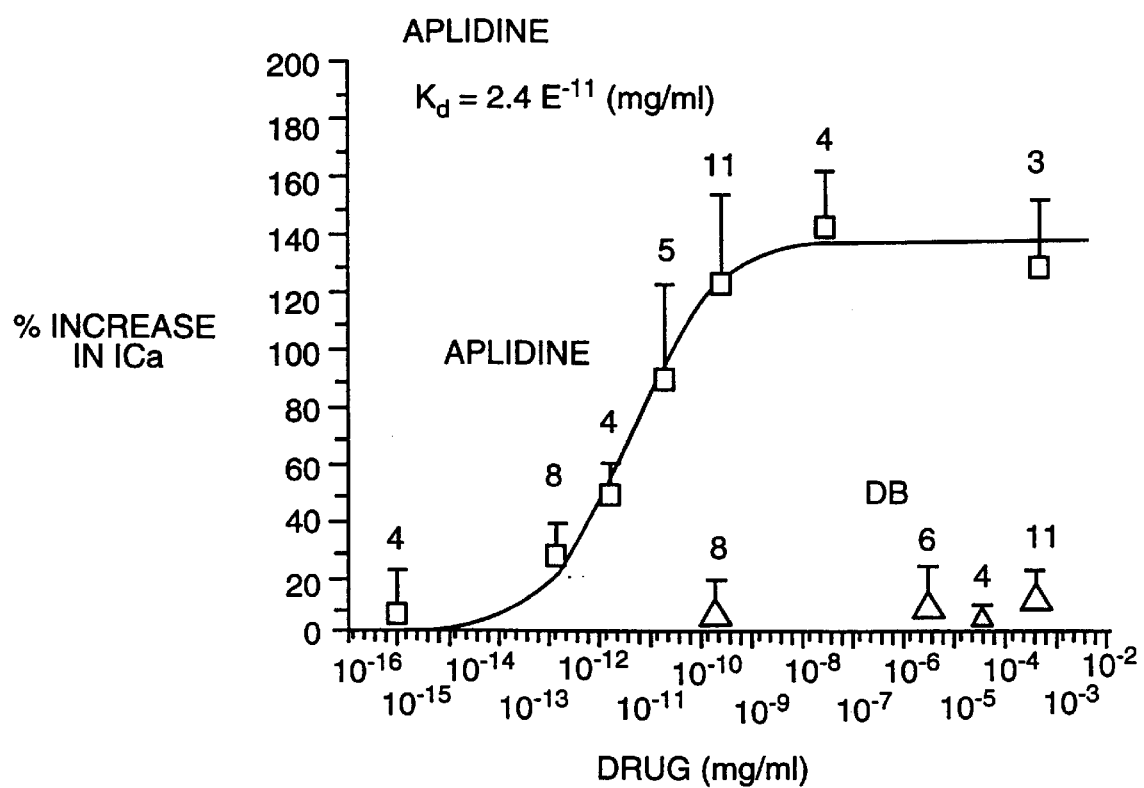
FIG. 2 is a composite dose-response curve comparing Aplidine and Didemnin B (DB) action on human atrial $I_{Ca}$. As illustrated, Didemniin B (DB) had no effect whereas Aplidine was highly effective, producing a very large increase in current amplitude.

To avoid rundown to currents, cells were exposed to varying concentrations of drug and group comparisons were made with cells not exposed to drug. The test results of Aplidine and Didemnin B are illustrated in FIGS. 1A, 1B and 2 accompanying this specification. As illustrated, Aplidine is far superior to Didemnin B (DB) and is a potent L-type calcium channel enhancer.

Aplidine may be administered by any number of routes, including the oral, sublingual, subcutaneous, intramuscular, intravenous, transdermal, and rectal routes. The compound is usually employed in the form of pharmaceutical compositions. Such compositions are prepared in a manner well known in the pharmaceutical art and comprise from about 1 to about 95 percent by weight of Aplidine.

Such pharmaceutical compositions comprise at least Aplidine as the active ingredient and a pharmaceutically acceptable carrier. In making such pharmaceutical compositions, the active ingredient will usually be mixed with a carrier, or diluted by a carrier, or enclosed within a carrier, which may be in the form of a capsule, sachet, paper or other container. When the carrier serves as a diluent, it may be a solid, semisolid or liquid material, which acts as a vehicle, excipient or medium for the active ingredient. Thus, the composition can be in the form of tablets, pills, powders, lozenges, sachets, cachets, elixirs, emulsions, solutions, syrups, suspensions, aerosols (as a solid or in a liquid medium), ointments containing for example up to 10% by weight of the active compound, soft and hard gelatin capsules, suppositories, sterile injectable solutions, and sterile packaged powders.

Some examples of suitable carriers, excipients, and diluents include lactose, dextrose, sucrose, sorbitol, mannitol, starches, gum acacia, calcium phosphate, alginates, calcium silicate, microcrystalline cellulose, polyvinylpyrrolidone, cellulose, tragacanth, gelatin, syrup, methyl cellulose, methyl- and propyl-hydroxybenzoates, talc, magnesium stearate, water, and mineral oil. The formulations can additionally include lubricating agents, wetting agents, emulsifying and suspending agents, preserving agents, sweetening agents or flavoring agents. The compositions may be formulated so as to provide quick, sustained, or delayed release of the active ingredient after administration to the patient by employing procedures well known in the art.

For oral administration, Aplidine can be admixed with carriers and diluents molded into tablets or enclosed in gelatin capsules. The mixtures can alternatively be dissolved in liquids such as ten percent aqueous glucose solution, isotonic saline, sterile water, or the like, and administered intravenously or by injection. Such solutions can, if desired, be lyophilized and stored in a sterile ampoule ready for reconstitution by the addition of sterile water for ready intramuscular injection.

The compositions are preferably formulated in a unit dosage form, each dosage containing an effective amount of one or more compounds of formula I, typically from about 1 to about 500 mg, more usually about 5 to about 300 mg, of the active ingredient. The term "unit dosage form" refers to physically discrete units suitable as unitary dosages for human subjects and other mammals, each unit containing a predetermined quantity of active material calculated to produce the desired therapeutic effect, in association with the required pharmaceutical carrier.

Aplidine is expected to be effective over a wide dosage range. For example, effective amounts of Aplidine will normally fall within the range of about 0.005 to about 50 mg/kg of body weight per day. In the treatment of adult humans, the range of about 0.001 to about 20 mg/kg, in single or divided doses per day, is preferred. However, it will be understood that the amount of the compound actually administered will be determined by a physician, in the light of the relevant circumstances including the condition to be treated, the choice of compound to be administered, the age, weight, and response of the individual patient, the severity of the patient's symptoms, and the chosen route of administration, and, therefore, the above dosage ranges are not intended to limit the scope of the invention in any way.

The present invention will be further illustrated with reference to the following examples, which aid in the understanding of the present invention, but which are not to be construed as limitations thereof. All percentages reported herein, unless otherwise specified, are percent by weight. All temperatures are expressed in degrees Celsius.

EXAMPLE 1

Extraction and Isolation of Natural Aplidine

A white solitary tunicate was collected near Ibiza in the Balearic Islands (Spain) and was identified by Dr. Xavier Turon of the Universitat de Barcelona, Barcelona (Spain) as *Aplidium albicans*. A sample is preserved at Centre d' Etudes Avancats, Blanes (Germona, Spain).

The frozen tunicate was extracted with methanol. Solvent partitioning of the residue afforded three active fractions, which were combined according to their similarity in TLC (Thin Layer Chromatography). The crude active fraction was portioned and the activity concentrated in the methanolic layer. The methanol layer was chromatographed by silica gel gravity column (chloroform and chloroform-methanol mixtures), affording one active fraction, which was further purified by Reversed-Phase High-Performance Liquid Chromatography (RPC$_{18}$HPLC), affording two peaks (I and II). Analysis by TLC revealed two identical spots in each HPLC fraction. Re-injection of each individual fraction led to two peaks with the same retention times as I and II. Co-injection of I and II confirmed the presence of two identical peaks (possible conformers) in each fraction suggesting a rapid interconversion of I to II and vice versa.

EXAMPLE 2

Semisynthesis of Aplidine from Didemnin A

Aplidine can also be obtained and its structure confirmed by comparison with a semisynthetic sample prepared by coupling of the appropriate side chain to natural didemnin A. The data obtained for the semisynthetic sample totally agreed with data for natural Aplidine.

2.1 Synthesis of Pyruvyl-Pro-OBzl

The hydrochloride salt of Pro-OBzl (10.2 g, 42 mmol) was dissolved in dry DMF (30 ml), neutralized with NMM (N-methylmorpholine, 4.7 mL, 42 mmol) at 0° C., and the solution was mixed with pyruvic acid (8.8 g, 100 mmol) and HOBt (1-hydroxybenzotriazole, 16.8 g, 110 mmol) in CH$_2$Cl$_2$-DMF (90 mL, 8:1). DCC (dicyclohexylcarbodiimide, 22.6 g, 110 mmol) in CH$_2$Cl$_2$ (35 mL) was added to the above mixture at 0° C. with stirring. The reaction mixture was stirred for 2 hours at 0° C. and left overnight at room temperature. DCCI was filtered off and washed with CH$_2$Cl$_2$ (20 mL). The filtrate was evaporated to dryness, the residue taken up in EtOAc and washed successively with 5% citric acid, water, 5% NaHCO$_3$ and finally with water to neutral pH. The organic layer was dried (Na$_2$SO$_4$) and concentrated. The residue was chromatographed on SiO$_2$ with hexane-EtOAc (2:1) to give the title compound (11 g, 95%).

$[\alpha]_D^{25}$=-78.57 (c 0.14, CHCl$_3$);

R$_f$=0.63 (19:1, CHCl$_3$/MeOH);

Anal. Calcd. for C$_{15}$H$_{18}$NO$_4$ (M+H): 276.1235;

Found: 276.1235 (M+H, HRFABMS).

2.2 Synthesis of Pyruvyl-Proline

The protected dipeptide from the previous synthesis (11.0 g, 40 mmol) was dissolved in EtOAc (75 mL) and stirred under hydrogen over Pd/C for 2 h. The catalyst was then filtered off and the filtrate was evaporated to dryness. The residue was crystallized from hexane to give the unprotected peptide (6.9 g, 93):

$[\alpha]_D^{25}$=-103.99 (c 0.124, CHCl$_3$);

R$_f$=0.4163 (19:1:0.5, CHCl$_3$/MeOH/AcOH;

Anal. Calcd. for C$_8$H$_{12}$NO$_4$ (M+H): 186.0766;

Found: 186.0765 (M+H, HRFABMS).

2.3 Synthesis of Aplidine

EDC (1-ethyl-3-(3-dimethylaminopropyl)carbodiimide, 4.27 g, 22.3 mmol) was added to a solution of Pyrvu-Pro (8.2 g, 44.5 mmol) in dry CH$_2$Cl$_2$ (40 mL) at 10° C. with stirring. The mixture was stirred for 2 h at 10° C. and then cooled to 0° C. Didemnin A (1.4 g, 1.48 mmol) in CH$_2$Cl$_2$-DMF (10 mL, 4:1) was added, and the clear solution was stirred at 0° C. for 2 h and then left in the refrigerator overnight.

DMAP (4-dimethylaminopyridine, 25 mg) was added to the reaction mixture, and it was again left in the refrigerator for 48 h. The solvent was evaporated to dryness, and the residue was taken up in EtOAc and washed with 5% NaHCO$_3$ and water to neutral pH. The organic layer was dried (Na$_2$SO$_4$) and concentrated. The residue so obtained was chromatographed on silica gel using CHCl$_3$-MeOH (19:1) to give Aplidine (1.4 g, 84%, 2 spots on TLC):

$[\alpha]_D^{25}$=-95.384 (c 0.06, MeOH)$_3$);

R$_f$=0.51 and 0.44 (19:1, CHCl$_3$/MeOH);

Anal. Calcd. for C$_{57}$H$_{88}$N$_7$O$_{15}$ (M+H): 1110.6338;

Found: 1110.6355 (M+H, HRFABMS).

The same series of reactions can be carried out with slight modifications; in particular EDC can be replaced by DDC with slightly lower yield.

The present invention has been described in detail, including the preferred embodiments thereof. However, it will be appreciated that those skilled in the art, upon consideration of the present disclosure, may make modifications and/or improvements on this invention and still be within the scope and spirit of this invention as set forth in the following claims.

What is claimed is:

1. A method of producing a cardiotonic effect in a patient in need thereof, which comprises administering to said patient the compound dehydrodidemnin B or a pharmaceutically acceptable salt thereof in an amount effective to produce said cardiotonic effect.

2. A method as claimed in claim 1 wherein said compound is administered in unit dosage form containing from about 0.01 to about 0.4 grams of said compound per kilogram of patient body weight per day.

3. A method as claimed in claim 2, wherein said unit dosage includes a biologically compatible excipient.

4. A method as claimed in claim 1, wherein said compound is administered parenterally.

5. A method as claimed in claim 4, wherein said compound is administered intravenously.

6. A method as claimed in claim 4, wherein said compound is administered intraperitoneally.

7. A method as claimed in claim 4, wherein said compound is administered intramuscularly.

8. A method as claimed in claim 4, wherein said compound is administered subcutaneously.

9. A method as claimed in claim 4, wherein said compound is administered transdermally.

10. A method as claimed in claim 1, wherein said compound is administered orally.

11. A method as claimed in claim 1, wherein said compound is administered in conjunction with an amount of beta-receptor agonist sufficient to produce a therapeutically effective increase in myocardial cAMP levels.

12. A method as claimed in claim 1, wherein said compound is administered in conjunction with an amount of phosphodiesterase inhibitor sufficient to produce a therapeutically effective increase in myocardial cAMP levels.

13. A method of treating congestive heart failure in a mammal in need thereof comprising administering to said mammal an effective amount of a compound of the formula:

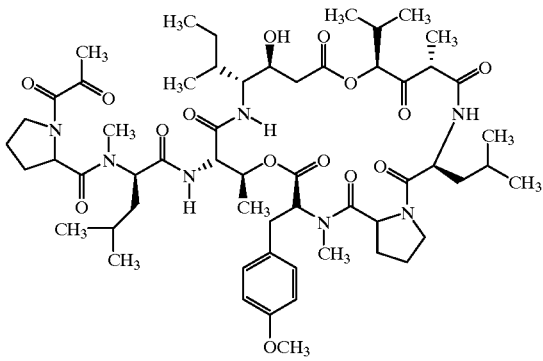

or pharmaceutically acceptable salts thereof.

14. A method for producing cardiotonic activity comprising administering to a patient in need of treatment an effective cardiotonic amount of a pharmaceutical composition comprising dehydrodidemnin B and a pharmaceutically acceptable carrier, diluent or excipient.

15. A method for treating congestive heart failure comprising administering to a patient in need of treatment an effective amount of a pharmaceutical composition comprising dehydrodidemnin B and a pharmaceutically acceptable carrier, diluent or excipient.

16. A method for prolonging the survival from heart failure in a patient suffering from cardiac insufficiency by administering to said patient the compound dehydrodidemnin B or a pharmaceutically acceptable salt thereof in an amount effective to improve cardiac contractile function in said patient.

17. The method of claim 16, wherein said compound is administered in unit dosage form containing from about 0.01 to about 0.4 grams of said compound per kilogram of patient body weight per day.

18. The method of claim 16, wherein said compound is administered in conjunction with an amount of beta-adrenergic receptor agonist sufficient to produce a therapeutically effective increase in myocardial cAMP levels.

19. The method of claim 16, wherein said compound is administered in conjunction with an amount of phosphodiesterase inhibitor sufficient to produce a therapeutically effective increase in myocardial cAMP levels.

20. The method of claim 16, wherein said compound is administered as a component of a nutritional product.

21. A method for prolonging the survival from heart failure in a patient suffering from insufficient cardiac contractile function comprising administering to said patient the compound dehydrodidemnin B or a pharmaceutically acceptable salt thereof in an amount sufficient to produce a cardiovascular agonist effect in said patient.

22. A method of producing a Class III antiarrhythmic effect for the treatment of atrial arrhythmias in a patient in need of such treatment, comprising administering to said patient the compound dehydrodidemnin B or a pharmaceutically acceptable salt thereof in an amount sufficient to produce a cardiovascular agonist effect in said patient.

* * * * *